United States Patent [19]

Dye et al.

[11] Patent Number: 5,405,402
[45] Date of Patent: Apr. 11, 1995

[54] IMPLANTABLE PROSTHESIS WITH RADIOGRAPHIC MARKER

[75] Inventors: Donald W. Dye, Pflugerville; Mark L. Arlitt, Austin, both of Tex.

[73] Assignee: Intermedics Orthopedics, Inc., Austin, Tex.

[21] Appl. No.: 48,416

[22] Filed: Apr. 14, 1993

[51] Int. Cl.⁶ .................... A61F 2/28; A61F 2/34
[52] U.S. Cl. .......................... 623/22; 623/16
[58] Field of Search ............ 623/16, 18, 19, 20, 623/22, 23

[56] References Cited

U.S. PATENT DOCUMENTS

| Re. 28,895 | 7/1976 | Noiles | 623/22 |
|---|---|---|---|
| 3,806,960 | 4/1974 | Weber | 623/22 |
| 3,829,904 | 8/1974 | Ling et al. | 623/22 |
| 3,891,997 | 7/1975 | Herbert | 623/22 |
| 3,922,726 | 12/1975 | Trentani et al. | 623/22 |
| 4,038,703 | 8/1977 | Bokros | 623/16 |
| 4,123,806 | 11/1978 | Amstutz et al. | 623/22 |
| 4,224,698 | 9/1980 | Hopson | 623/22 |
| 4,450,592 | 5/1984 | Niederer et al. | 623/22 |
| 4,695,282 | 9/1987 | Forte et al. | 623/22 |
| 5,032,129 | 7/1991 | Kurze et al. | 623/23 |
| 5,035,714 | 7/1991 | Willert et al. | 623/23 |
| 5,219,363 | 6/1993 | Crowninshield et al. | 623/23 |

*Primary Examiner*—David Isabella
*Attorney, Agent, or Firm*—Richard L. Robinson

[57] ABSTRACT

An implantable prosthesis comprises a polyethylene prosthetic member that is substantially transparent to x-rays and a radiographic marker that is substantially opaque to x-rays. The radiographic marker is configured as a tension spring arranged as a continuous ring encircling the prosthetic member.

15 Claims, 2 Drawing Sheets

IMPLANTABLE PROSTHESIS WITH RADIOGRAPHIC MARKER

BACKGROUND OF THE INVENTION

1. Field of the invention

This invention relates generally to implantable prostheses for human joint replacement, and relates more particularly to implantable prostheses that are not readily visible in x-ray radiographs and therefore require a radiographic marker.

2. Background information

Implantable orthopedics prostheses for human joint replacement are sometimes composed of materials which are substantially transparent to x-rays and which therefore do not show well on radiographs of the implanted prosthesis. One such material is high-density polyethylene which is often used as a bearing surface in orthopedic prostheses.

It is sometimes desirable to fashion an orthopedic implant entirely from polyethylene. Examples of such prostheses are all-poly cemented acetabular cups, and all-poly cemented shoulder glenolds. To permit radiographic examination of all-poly prostheses once implanted, it is known to provide a wrap of wire about the periphery of the prothesis. The wire is substantially opaque to x-rays and therefore will be easily visible on a radiographic view of the implanted prosthesis.

One known arrangement for providing a radiographic marker wire on, for example, an acetabular cup, involves wrapping a wire about the periphery of the cup near the opening such that the wire is received in an annular groove in the polyethylene material of which the cup is made. The ends of the wire are provided with a 90° bend and are received in radially inwardly directed holes in the outer surface of the polyethylene cup. Engagement of the bent ends of the radiographic marker wire with the receiving holes of the cup prevent the wire from dislodging and becoming unwrapped.

As one can readily appreciate, the length of the marker wire must be precision cut to length so that the ends properly engage the holes when the wire is wrapped about the circumference of the cup. Furthermore, each size or diameter of acetabular cup requires a correspondingly sized marker wire, which multiplies the number of components that must be stocked in order to assemble all-poly prostheses of various sizes. It is also readily apparent that assembling the marker wire to the prosthesis can be a tedious and relatively time consuming operation.

It would be desirable to provide an all-poly orthopedic prosthesis that can be manufactured in different sizes without requiring a different sized radiographic marker for each prosthesis. It would also be desirable to provide an all-poly orthopedic prosthesis to which the radiographic marker can be easily and quickly attached.

SUMMARY OF THE INVENTION

It is an object of the present invention to provide implantable protheses that satisfy the desires set forth above. Other objects and advantages of the invention will be apparent from the following description and drawings.

In accordance with one aspect of the present invention, an implantable prosthesis is provided having a prosthetic member that is substantially transparent to x-rays, and a radiographic marker that is substantially opaque to x-rays. The radiographic marker is configured as a tension spring arranged as a continuous ring encircling the prosthetic member.

In accordance with another aspect of the present invention, a set of implantable prostheses of different sizes is provided from which one implantable prosthesis sized appropriately for a patient's anatomy is selected for implantation. The set of implantable prostheses includes a plurality of prosthetic members in different sizes that are substantially transparent to x-rays. Also included is a single radiographic marker that is substantially opaque to x-rays. The radiographic marker is configured as a tension spring arranged as a continuous ring for encircling a selected one of the plurality of prosthetic members. The radiographic marker has sufficient spring elasticity to permit it to be elastically expanded in diameter for assembly to any one of the plurality of prosthetic members, and thereafter decrease in diameter under tension for retention thereon.

DESCRIPTION OF THE PREFERRED EMBODIMENTS

Figure 1:
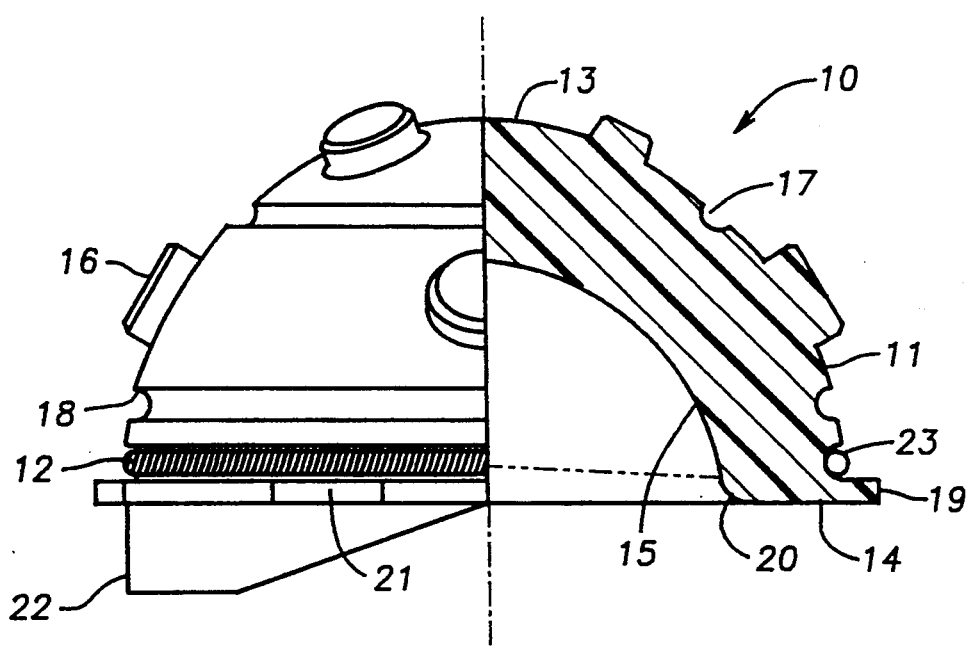
FIG. 1 is a partially sectioned side elevation view of an all-poly implantable orthopedic prosthesis, namely an acetabular cup, constructed in accordance with the present invention, and including a tension spring radiographic marker.
Figure 2:
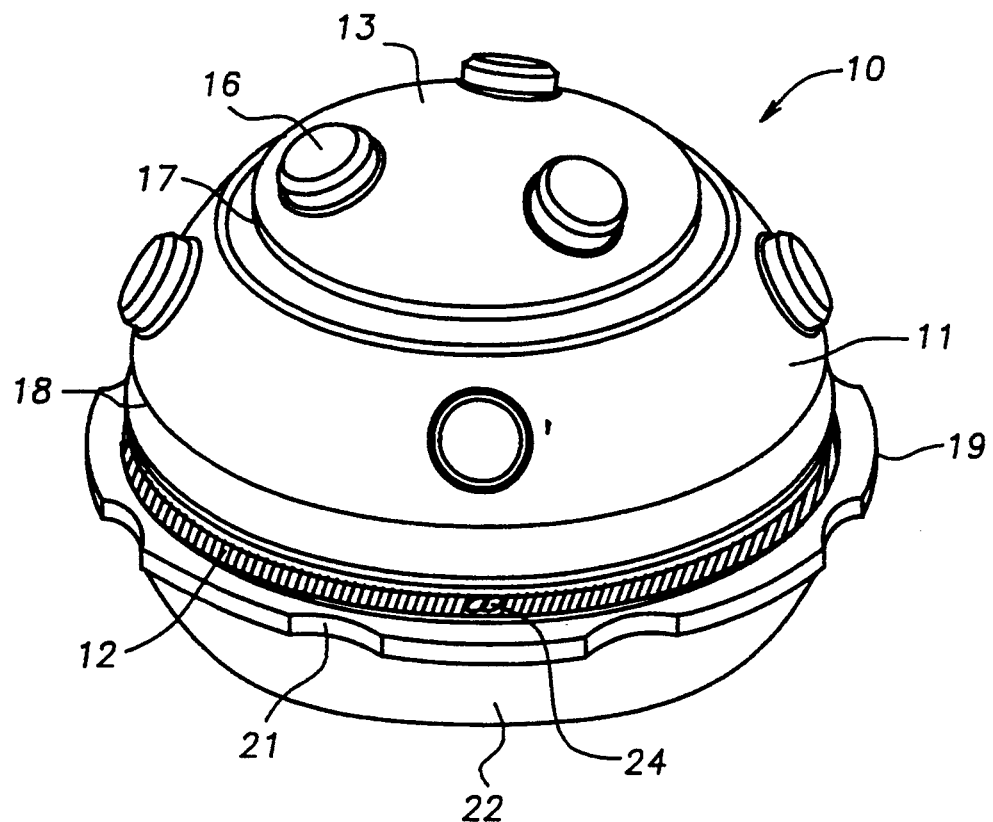
FIG. 2 is a perspective view of the all-poly acetabular cup of FIG. 1.

Referring in particular to FIGS. 1 and 2, there is illustrated an implantable prosthesis 10 including a prosthetic member 11 and a radiographic marker 12. In the illustrated embodiment, prosthetic member 11 is configured as an acetabular cup constructed of high density polyethylene. Prosthetic member 11 is generally configured as a hemispherical cup having a spherical outer surface 13, a rim 14, and a cavity 15 for receipt of the head of a femoral component (not shown). Outer surface 13 of prosthetic member 11 has a plurality of round pegs 16 projecting normally from the surface thereof and distributed over the surface in spaced relationship. Outer surface 13 also includes a pair of annular grooves 17 and 18 oriented substantially parallel to rim 14. Pegs 16 and annular grooves 17 and 18 serve to interlock prosthetic member 11 with the cement mantel overlying outer surface 13 and disposed between prosthetic member 11 and the reamed out acetabulum of the patient. Pegs 16 also act as cement spacers to position outer surface 13 of prosthetic member 11 at an appropriate distance from the reamed out acetabulum such that the cement mantel is substantially uniform in thickness. Rim 14 includes a flange 19 extending radially outwardly from the opening 20 of prosthetic member 11 defined by the intersection of rim 14 and cavity 15. Flange 19 serves to retain and compress cement within the acetabulum as prosthetic member 11 is pressed in place, and is provided with a plurality of scalloped cut-outs 21 distributed evenly about the circumference of flange 19. Cut-outs 21 provide for the escape of excess bone cement extruded therethrough as prosthetic member 11 is pressed into the cement mantel in the acetabulum. Prosthetic member 11 also includes hood 22 extending axially from rim 14 on only one side of prosthetic member 11. Hood 22 provides additional retention of the ball of the femoral component in a direction selected by the physician at the time of implantation of prosthetic member 11. Outer surface 13 of prosthetic member 11 is provided with an area of differential surface elevation immediately adjacent flange 19 on the cement receiving side of the flange. In particular, the area of differential surface elevation includes an annular groove 23 in which is received radiographic marker 12.

Radiographic marker 12 comprises a tension coil spring wound of stainless steel wire and joined at its ends to form a continuous ring encircling prosthetic member 11. Joint 24 of radiographic marker 12 is preferably aligned with a selected portion of the prosthetic member, in this case the hood 22. Joint 24 comprises an area on radiographic marker 12 having a different radiographic density from the remainder of radiographic marker 12. The density of joint 24 can be either greater than or less than the density of the rest of radiographic marker 12, and can be provided either by a weld joining the ends of the coil spring, or interlocked loops at the ends of the coil spring, or by any other joinder means providing differential density. By aligning joint 24 with a selected portion of the prosthetic member 11 it is possible to radiographically mark the orientation of the selected portion when the implantable prosthesis 10 is implanted. Of course, if the all-poly prosthesis is symmetrical, or if it is otherwise not necessary or desirable to indicate its orientation, the provision of a joint of differential density is optional.

Radiographic marker 12 is constructed with sufficient spring elasticity to permit it to be elastically expanded in diameter so as to pass over outer surface 13 and pegs 16, and thereafter decrease in diameter under tension for receipt and retention within annular groove 23. Alternatively, radiographic marker 12 could be passed in its expanded configuration over flange 19 into annular groove 23. The depth of annular groove 23 relative to outer surface 13, i.e., the differential surface elevation, is more than 50% of the coil diameter of radiographic marker 12. This depth has been found to be sufficient to reliably retain radiographic marker 12 on prosthetic member 11. Grooves of greater or lesser depth may also be suitable, depending upon the configuration of the prosthetic member.

One advantage of the present invention is that radiographic marker 12 is constructed with sufficient spring elasticity to permit it to be elastically expanded in diameter for assembly to any one of a set of prosthetic members 11 manufactured in different sizes, i.e., diameters. Thus, it is possible to provide a set of implantable prostheses in different sizes from which one implantable prostheses that is sized appropriately for a patient's anatomy is selected. It is only necessary to manufacture radiographic marker 12 in one size to fit all of the differently sized prosthetic members comprising the set of implantable prostheses. Assembly of radiographic marker 12 to prosthetic member 11 can be done quickly and easily by hand, or with an appropriate expanding tool such as a cone received over the spherical outer surface 13 of prosthetic member 11.

Prosthetic member 11, being constructed of high-density polyethylene, is substantially transparent to x-rays. Radiographic marker 12, on the other hand, is constructed of any biologically compatible metal having the necessary elastic characteristics, but preferably 316L stainless steel, that is substantially opaque to x-rays.

Figure 3:
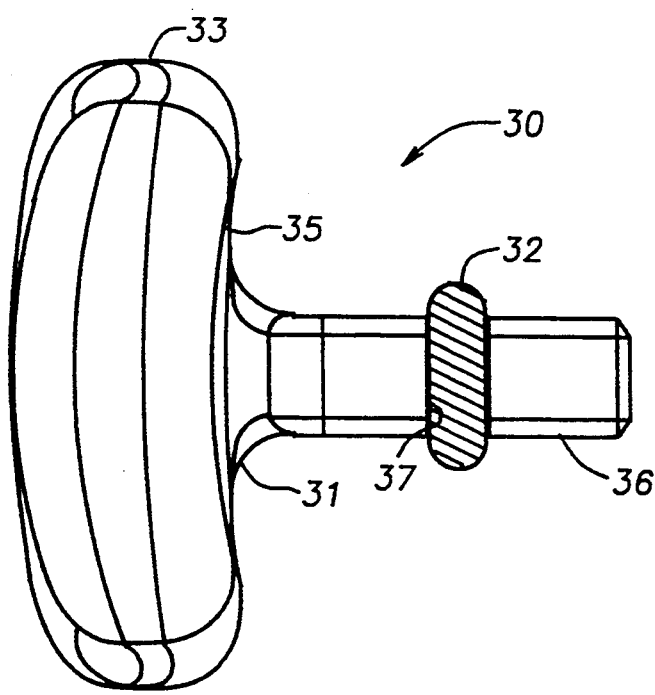
FIG. 3 is a top view of an alternative embodiment of an all-poly implantable orthopedic prosthesis, namely a shoulder glenold, constructed in accordance with the present invention, and including a tension spring radiographic marker.
Figure 4:
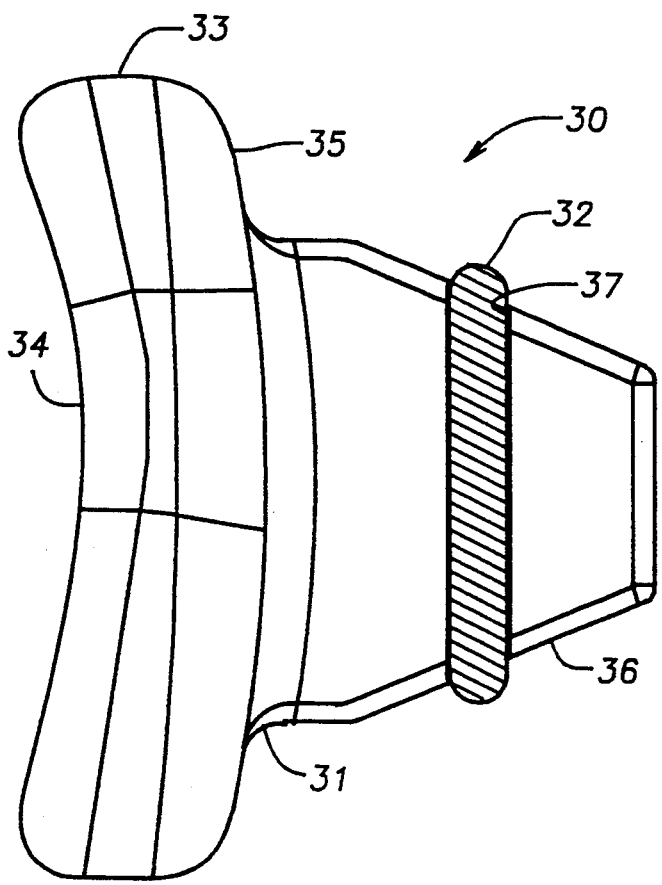
FIG. 4 is a side elevation view of the all-poly shoulder glenold of FIG. 3.

Referring to FIGS. 3 and 4, there is illustrated another embodiment of the present invention in the form of implantable prosthesis 30 including a prosthetic member 31 and a radiographic marker 32. Prosthetic member 31 is configured as a shoulder glenoid constructed of high density polyethylene. Prosthetic member 31 includes a generally oval member 33 having a convex lateral surface 34 serving as the articular surface. Extending from medial surface 35 of oval member 33 is a trapazoidally shaped keel 36. A groove 37 circumscribes keel 36 transverse thereto. Radiographic marker 32 comprises a tension coil spring wound of stainless steel wire and joined at its ends to form a continuous ring encircling keel 32 of prosthetic member 31. Marker 32 is constructed with sufficient spring elasticity to permit it to be elastically expanded in diameter so as to pass over keel 36, and thereafter decrease in diameter under tension for receipt and retention within groove 37. The depth of groove 37 relative to the outer surface of keel 36, i.e., the differential surface elevation, is more than 50% of the coil diameter of radiographic marker 32. This depth has been found to be sufficient to reliably retain radiographic marker 32 on prosthetic member 31. Grooves of greater or lesser depth may also be suitable, depending upon the configuration of the prosthetic member.

Figure 5:
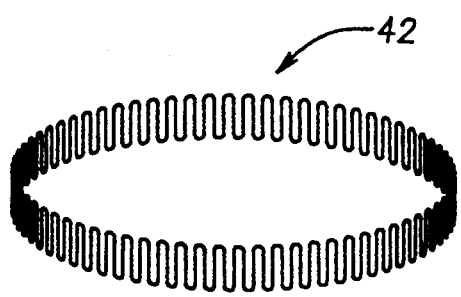
FIG. 5 is a perspective view of an alternative embodiment of a tension spring radiographic marker for use in connection with the present invention, wherein the marker is configured as a serpentine spring.

Referring in particular to FIG. 5, there is illustrated an alternative embodiment of a radiographic marker 42 for use with a prosthetic member as described herein. Radiographic marker 42 retains the essential characteristic of a tension spring arranged as a continuous ring, like radiographic markers 12 and 32, but rather than being wound as a coil, it is configured as a serpentine spring. This embodiment illustrates that the radiographic marker can assume other configurations without departing from the spirit of the present invention, so long as the marker has the characteristics of a tension spring, i.e., it is elastically expandable in circumference.

While the present invention has been described in terms of preferred embodiments as shown in the drawings, the scope of the invention is not limited to such embodiments but only by the terms of the claims appended below.

What is claimed is:

1. An implantable prosthesis comprising:
    a prosthetic member that is substantially transparent to X-rays; and
    a radiographic marker that is substantially opaque to X-rays, said radiographic marker being configured as a tension spring arranged as an unbroken, non-overlapping continuous ring encircling said prosthetic member,
    said prosthetic member including an outer surface having areas of differential surface elevation for receiving and retaining said radiographic marker against movement in a direction generally perpendicular to the ring of the radiographic marker and generally parallel to the outer surface of the prosthetic member.

2. The implantable prosthesis of claim 1, in which said areas of differential surface elevation comprise a groove in the outer surface at least partially circumscribing the prosthetic member.

3. The implantable prosthesis of claim 2, in which said groove is substantially annular.

4. The implantable prosthesis of claim 2, in which said groove is substantially continuous.

5. The implantable prosthesis of claim 1, in which said radiographic marker differs in radiographic density about its circumference to provide X-ray detection of the orientation of the implantable prosthesis.

6. The implantable prosthesis of claim 5, in which said radiographic marker has a joint at which ends of the tension spring are joined to form a ring, said joint comprising an area of differential radiographic density.

7. The implantable prosthesis of claim 1, in which said radiographic marker has sufficient spring elasticity to permit it to be elastically expanded in diameter for assembly to said prosthetic member, and thereafter decrease in diameter under tension for retention thereon.

8. An implantable prosthesis comprising:
   a prosthetic member that is substantially transparent to X-rays; and
   a radiographic marker that is substantially opaque to X-rays, said radiographic marker being configured as a tension spring arranged as an unbroken, non-overlapping continuous ring encircling said prosthetic member, said radiographic marker having sufficient spring elasticity to permit it to be elastically expanded in diameter for assembly to said prosthetic member, and thereafter decrease in diameter under tension for retention thereon, said radiographic marker being comprised of biologically compatible wire configured as a coil spring.

9. The implantable prosthesis of claim 8, in which said radiographic marker is comprised of stainless steel.

10. The implantable prosthesis of claim 7, in which said radiographic marker is comprised of biologically compatible wire configured as a serpentine spring.

11. The implantable prosthesis of claim 10, in which said radiographic marker is comprised of stainless steel.

12. A set of implantable prostheses in different sizes from which one implantable prosthesis sized appropriately for a patient's anatomy is selected for implantation, comprising:
   a plurality of prosthetic members in different sizes that are substantially transparent to X-rays; and
   only one radiographic marker that is substantially opaque to X-rays, said radiographic marker being configured as a tension spring arranged as an unbroken, non-overlapping continuous ring for encircling a selected one of said plurality of prosthetic members, said radiographic marker having sufficient spring elasticity to permit it to be elastically expanded in diameter for assembly to any one of said plurality of prosthetic members, and thereafter decrease in diameter under tension for retention thereon;
   said prosthetic member including an outer surface having areas of differential surface elevation for receiving and retaining said radiographic marker against movement in a direction generally perpendicular to the ring of the radiographic marker and generally parallel to the outer surface of the prosthetic member.

13. The implantable prosthesis of claim 12, in which said areas of differential surface elevation comprise a groove in the outer surface at least partially circumscribing the prosthetic member.

14. A set of implantable prostheses in different sizes from which one implantable prosthesis sized appropriately for a patient's anatomy is selected for implantation, comprising:
   a plurality of prosthetic members in different sizes that are substantially transparent to X-ray; and
   only one radiographic marker that is substantially opaque to X-rays, said radiographic marker being configured as a tension spring arranged as an unbroken, non-overlapping continuous ring for encircling a selected one of said plurality of prosthetic members, said radiographic marker having sufficient spring elasticity to permit it to be elastically expanded in diameter for assembly to any one of said plurality of prosthetic members, and thereafter decrease in diameter under tension for retention thereon, said radiographic marker differing in radiographic density about its circumference to provide X-ray detection of the orientation of the implantable prosthesis, said radiographic marker having a joint at which ends of the tension spring are joined to form a ring, said joint comprising an area of differential radiographic density, said radiographic marker being comprised of biologically compatible wire configured as a coil spring.

15. The implantable prosthesis of claim 14, in which said radiographic marker is comprised of biologically compatible wire configured as a serpentine spring.

* * * * *